Figure 1:
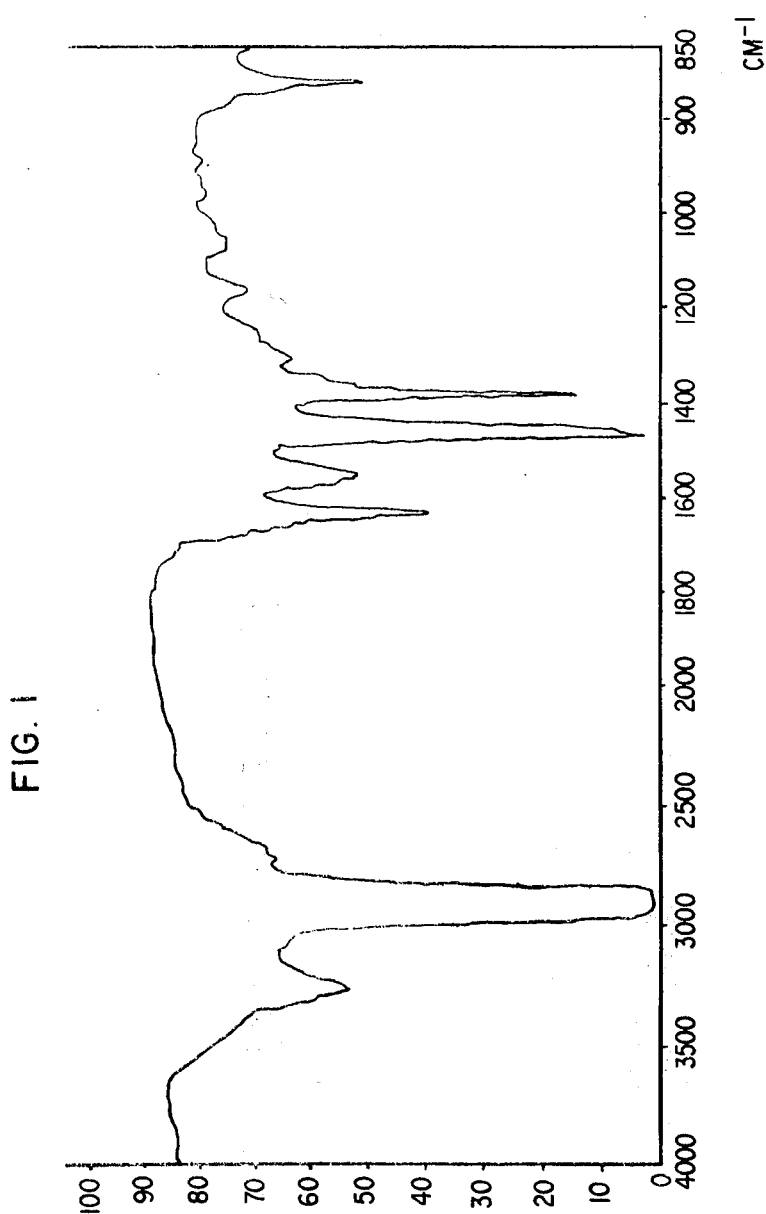

United States Patent [19]

Kuwana et al.

[11] 4,050,989
[45] Sept. 27, 1977

[54] PROCESS OF PREPARING DESACYL-PEPSIDINE WITH *BACILLUS PUMILUS*

[75] Inventors: Noriaki Kuwana, Inuyama; Yoshikazu Hasegawa, Kounan; Yukio Nozu, Gifu, all of Japan

[73] Assignee: Eisai Co., Ltd., Tokyo, Japan

[21] Appl. No.: 673,883

[22] Filed: Apr. 5, 1976

Related U.S. Application Data

[62] Division of Ser. No. 638,093, Dec. 5, 1975.

[30] Foreign Application Priority Data

Dec. 5, 1974  Japan .................................. 49-138862

[51] Int. Cl.² .............................................. C12D 13/06
[52] U.S. Cl. ........................................ 195/29; 195/96

[58] Field of Search ................... 195/29, 80 R, 65, 96

[56] References Cited

U.S. PATENT DOCUMENTS

| | | | |
|---|---|---|---|
| 3,819,486 | 6/1974 | Murao et al. ...................... | 195/80 R |
| 3,907,638 | 9/1975 | Uzuki et al. ............................ | 195/29 |

*Primary Examiner*—Lionel M. Shapiro
*Attorney, Agent, or Firm*—Wenderoth, Lind & Ponack

[57] ABSTRACT

Novel desacyl-pepsidine and process for the preparation thereof comprising contacting N-acyl-pentapeptide with a bacterium which belongs to *Bacillus pumilus*. The new compounds are useful as pepsin-inhibitor and as intermediates for the preparation of N-acyl-pentapeptide homologues.

9 Claims, 1 Drawing Figure

PROCESS OF PREPARING DESACYL-PEPSIDINE WITH *BACILLUS PUMILUS*

This is a division of application Ser. No. 638,093, filed Dec. 5, 1975.

The present invention relates to novel desacyl-pepsidine (hereinafter referred to DA-pepsidine).

The novel DA-pepsidine according to the present invention is a pentapeptide, i.e. valyl-valyl-4-amino-3-hydroxy-6-methyl-heptanoyl alanyl-4-amino-3-hydroxy-6-methyl-heptanoic acid having the formula (I):

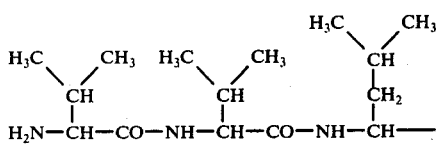
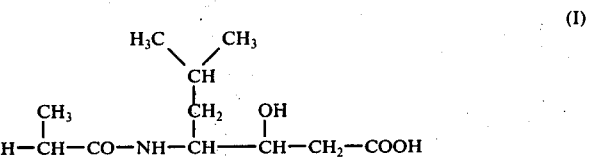

(I)

DA-pepsidine possesses a strong pepsin-inhibitory activity and thus may be useful for treating the subject suffering from gastric ulcer.

Further, the present invention relates to a process for the preparation of DA-pepsidine which comprises contacting N-acyl-peptapeptide with a bacterium belonging to *Bacillus pumilus*.

N-acyl-pentapeptide used as the starting material in the present invention is a pentapeptide, i.e. N-acyl-valyl-valyl-4-amino-3-hydroxy-6-methyl-heptanoyl-alanyl-4-amino-3-hydroxy-6-methyl-heptanoic acid having the formula (II):

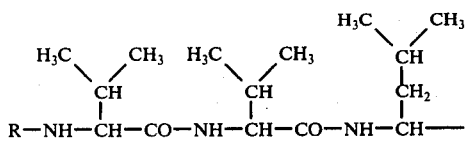
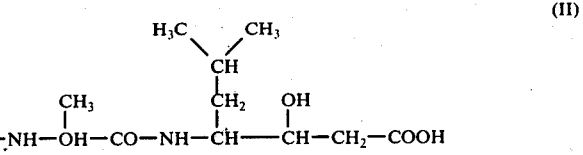

(II)

wherein R is an acyl group.

As N-acylpentapeptide (II), there are already known more than ten compounds. The compound wherein R is acetyl group, for example, has been discovered by N. Kuwana (one of the coinventors of the present invention) et al, as described in U.S. Pat. Nos. 3,819,486 and 3,878,185, and Japanese patent application No. 39,446/73 wherein the said compound has been referred to "S-PI" or "Pepsidine C". In Japanese patent application no. 39446/73, there are disclosed the compounds wherein R is butyryl and propionyl group, as "Pepsidine A" and "Pepsidine B," respectively.

On the other hand, there are disclosed the N-acyl-pentapeptides wherein R is isovaleryl group or straight or branched aliphatic acyl group having 5 to 16 carbon atoms, by Umezawa et al in Japanese Patent Publication No. 8996/72, Japanese Patent Laid-open No. 29582/72 and Japanese Patent Laid-open No. 41590/74, wherein the said compounds have been referred to "Pepstatin."

It is known that these known N-acyl-peptapeptides have a strong pepsin-inhibitory activity.

N-acyl-pentapeptides are provided by cultivation of various Actinomycetes. Above mentioned pepsidines, for example, are provided by cultivation of *Streptmyces naniwaensis* EF 44-201 strain. And, the pepstatins are provided, for example, by cultivation of *Streptomyces testaceus*. However, N-acyl-pentapeptides provided by the cultivation of these Actinomycetes are usually not homogeneous, but a mixture of several or more than ten N-acyl-pentapeptides having various acyl moieties (R) and similar properties. Thus, in order to provide particular N-acyl-pentapeptide, there are required very complicated processes for separating, whereby the yield of the desired product may be considerably reduced.

DA-pepsidine having free N-terminal has the fundamental structure in common with above N-acyl-pentapeptide homologues. Thus, when DA-pepsidine is first prepared according to this invention using the mixture of various N-acyl-pentapeptides obtained by the cultivation of above *Streptomyces* strain, and the the resulting DA-pepsidine is acylated by particular acylating agent, the desired sole N-acyl-pentapeptide is obtained easily.

Further, DA-pepsidine may be useful as an intermediate for the synthesis of other N-acyl-pentapeptide homologues as yet unknown.

A strain preferable for the present invention is *Bacillus* EF 49-210 (nov. sp.) strain, which was separated from the soil at Kawaguchiko machi, Yamanashi Prefecture, Japan. The microbiological properties for the strain are shown as follows:

I. Microscopic observation (bouillon agar nutrient medium)

1. Morphologies: Rods with rounded ends, occuring single or in pairs or rarely in three combination.
2. Size: 0.4 to 0.7 by 1.0 to 4.0 microns.
3. Motility: Motile.
4. Flagella: Paritrichous
5. Spores: Formed
6. Gram stain: Positive
7. Acid fast stain: Negative II. Cultivation View 1. Bouillon agar slant medium (at 30° for 1 day)
   Growth spreading flat, milky yellowish to slightly yellowish, and weakly lustered. No change in color of nutrient medium.
2. Bouillon agar flat medium (at 30° C for 1 - 7 days)
   Growth spreading flat, dendroid, milky yellowish; slightly yellowish, smooth colony, weakly lustered and translucent to opaque. No soluble pigment.
3. Broth medium (at 30° C for 2 days)
   Formed pellicle on surface. Turbidity is weak and uniform.
4. Gelatin medium (at 20°, 27° and 30° C for 3 days)
   Growth weakly, but liquefies the gelatin. It is not clear by stab cultare.
5. Litmus milk (at 30° C for 6 days)

Rather acidic, and weakly liquefied after 6 day cultivation. No coagulation.
6. Potato (at 30° C for 2 days)
Growth wet and spreading slimy. Potato darkened.

III. Physiological Properties.

| | | |
|---|---|---|
| 1. | Nitrate reduction property | Negative |
| 2. | Denitrogen reaction | Negative |
| 3. | Methyl red test | Positive |
| 4. | Voges-Proskauer reaction | Positive |
| 5. | Formation of indole | Negative |
| 6. | Formation of hydrogen sulfide | Negative |
| 7. | Hydrolysis of starch | Negative |
| 8. | Utilization of citric acid | Positive in Koser's medium Negative in Symmon's medium |
| 9. | Utilization of the source of inorganic nitrogen: Weakly positive with potassium nitrate. Weakly positive with ammonium sulfate. | |
| 10. | Formation of pigment | Negative |
| 11. | Urease | Negative |
| 12. | Oxidase | Positive |
| 13. | Catalase | Positive |
| 14. | Range of growth: a) pH (broth nutient medium at 30° C for 2 days with shaking) Growth in sterilized medium at pH 5 to 9.8. b) Temperature (broth nutient medium for 2 days with shaking) Growth at 20° C to 45° C. c) Concentration of salt (broth nutrient medium for 2 days with shaking) Growth within one day, in the concentration 7.0% of NaCl. Growth within two days, in the concentration of 10% of NaCl. | |
| 15. | Oxygen requirement | Facultative anaerobic. |
| 16. | O-F test by Hugh-Leifson method: Acid is formed in both aerobic and anaerobic. No gas formed. | |
| 17. | Fermentation test and acid formation with carbohydrates are as follows: | |

| | | Acid formation | |
|---|---|---|---|
| No. | Carbohydrates | aerobic | anaerobic |
| 1 | arabinose | − | ± |
| 2 | xylose | ± | ± |
| 3 | glucose | + | + |
| 4 | mannose | + | + |
| 5 | fructose | + | + |
| 6 | galactose | ± | ± |
| 7 | maltose | − | ± |
| 8 | sucrose | + | + |
| 9 | lactose | − | ± |
| 10 | trehalose | + | + |
| 11 | sorbitol | − | ± |
| 12 | mannitol | − | ± |
| 13 | inositol | + | + |
| 14 | glycerol | + | ± |
| 15 | starch | − | ± |

No gas formed in any of the carbohydrate.
Acid (+), Slight acid (±), No acid (−).

By comparing the data of the above mentioned properties of the bacterium with those described in Bergey's Manual of Determinative Bacteriology, the seventh edition, this bacterium is considered to be a variant of *Bacillus pumilus*, and the said bacterium was nominated as *Bacillus pumilus Kawaguchi*. This bacterium EF49-210 (ATCC No. 31132) strain has been deposited at the Agency of Industrial Science and Technology, Fermentation Research Institute in Japan as FERM-P No. 2677. It was also recognized that there is suitably used for the object of the present invention the known bacterium *Bacillus pumilus* IFO-12092 and IFO-12110 which are stored in Institute of Fermentation Osaka in Japan.

In the cultivation of the microorganisms to be used in the present invention, there may be used any composition of the nutrient medium and any conditions for the cultivation, provided that the microorganisms can grow, and fully exhibit desired activities. There may be selected, the medium containing for example, any organic or inorganic nitrogen sources such as peptone, meat extract, corn steep liquor, soy-bean hydrolyzate, soy-bean extract, yeast extract, inorganic ammonium salts and the like; any carbon sources such as molasses, dextrose, starch and hydrolysis product thereof; and inorganic salts. The cultivation is generally carried out with shaking or aerating at a temperature ranging from 20° to 45° C for a period of time from one to seven days.

It was found that the deacylating activity of the *Bacillus pumilus* exists both intra- and extra-cellularly. Thus, in the practice of this invention, there may be used culture broth, culture filtrate, whole cells, dry cells and/or enzyme preparations obtained therefrom.

The starting material of the present invention, N-acyl-pentapeptide, is not always required to use in a purified form. There may be used, for example, a mixture of several N-acyl-pentapeptides-containing which may be obtained in various purification stage such as culture filtrate of the microorganism which produces N-acyl-pentapeptides, and products salted out from said culture filtrate. The products obtained by the culture filtrate with an organic solvent and then removing the solvent may also be used.

In practice of the present invention, the reaction conditions such as concentration, temperature, pH, and the like are not critical and can be varied over broad range depending upon the kinds of the strain of microorganisms used and the N-acyl-pentapeptide selected as the starting material. When deacylation of N-acyl-pentapeptide is carried out by using *Bacillus pumilus* Kawaguchi EF 49-210 strain, for example, it is preferable to use a condition in the range of pH 4 to 10, at a temperature of about 30° − 50° C. The reaction time of the range from 3 to 60 hours is suitable. By addition of $Co^{++}$ compound such as $CoCl_2$, $CoSO_4$ etc., the yield of DA-pepsidine may be increased.

Separation and purification of DA-pepsidine from the reaction mixture can be carried out using any conventional procedure such as solvent extraction, column chromatography, fractional crystallization, recrystallization, and the like.

To detect the formation of DA-pepsidine of the present invention, thin layer chromatography can be used as follows:

Sample solution is spotted on a thin layer plate of Silica Gel G (manufactured by Merck A. G.; Trademark), and developed with a mixed solvent (I) containing n-butyl alcohol, acetic acid and water in the ratios by volume of 3 : 1 : 1, or a mixed solvent (II) containing n-butyl alcohol, acetic acid, water and n-butyl-acetate in the ratios by volume of 4 : 1 : 1 : 4. DA-pepsidine is detected as a spot which is positive in the ninhydrin reaction and also Rydon-Smith reaction, at Rf = 0.48 in the case of the use of the mixed solvent (I).

Alternatively, it is detected by Casein plate method as follows:

After the developed and dried thin layer plate mentioned above is transferred to a flat board of Casein-containing agar, a filter paper impregnated with pepsin solution is placed on the board. Reaction is then effected at 30° C for overnight, to detect a non-decomposed casein.

DA-pepsidine of the present invention has the following physio-chemical properties:

i. Appearance: White needles
ii. Solubility: Easily soluble in acetic acid and methanol; soluble in ethanol, n-butanol and pyridine; and slightly soluble in acetone and ethylether.

iii. Coloring reaction: Positive in both ninhydrine reaction and Rydon-Smith reaction.

iv. Ultraviolet absorption spectrum: 0.1% methanol solution exhibits only the end absorption due to the peptide bone, but no maximum absorption is shown in the region from 250 mμ to 370 mμ.

v. Infrared absorption spectrum: Refer to the accompanying FIG. 1.

vi. Composition of amino acid: After hydrolysis with 6N HCl for 72 hours at 110° C, the sample was analyzed by means of amino acid analyzer. It is confirmed that the molar ratio of alanine and valine is 1 : 2.

vii. Molecular weight and structural formula: Sample was acetylated by acid chloride method, followed by methyl-esterification by diazo methane method. The resulting compound was subjected to mass spectrum analysis and determined to $M^+ = 657$. Thus, the molecular weight of the sample was identical with the calculation value 601 of DA-pepsidine. The peak of fragment was also identical with the calculation value derived from the structural formula (I) of DA-pepsidine. In addition, aforementioned acetylated product of the sample was identical with pepsidine C on thin layer chromatography, and the esterified product was also identical with methyl ester of pepsidine C.

viii. Pepsin-inhibitory activity: Pepsin-inhibitory activity of DA-pepsidine was determined using the method reported by S. Murao and S. Satoi in Agr. Biol. Chem. Japan 34 (8) 1265 – 7 (1970). It was shown that the amount of DA-pepsidine which gives 50% inhibition against 100 μg of pepsin is 0.82 μg. While, that of pepsidine C is 0.86 μg.

Following examples are given to illustrate the preferred embodiment of the present invention, without limiting the scope of this invention.

EXAMPLE 1

Into 0.5 liter Sakaguchi flask, there was charged 0.1 liter of liquid medium (pH 7) containing 1% of meat extract, 1% of peptone and 0.5% of NaCl, and the medium was sterilized at 120° C for 10 minutes.

Each of the 20 flasks prepared as above was inoculated respectively by 1 ml of the broth of *Bacillus Pumilus* Kawaguchi EF 49-210 strain which was cultivated previously on the similar nutrient medium at the temperature of 30° C for 24 hours and cultivated with shaking at 30° C for 72 hours.

After the completion of the cultivation, the cells were removed from the broth by centrifugation, and to the combined supernatant 4 liters of cold acetone were added dropwise under cooling. The resulting precipitate was suspended in distilled water to provide 50 ml of suspension. On the other hand, 10 g of N-acyl-pentapeptide mixture (pepsidine C, pepsidine B and pepsidine A in the ratio by weight of 94 : 4 : 2) were dissolved into water and 6N NaOH was added to neutralize, thereby providing 500 ml of aqueous solution. Into an aqueous solution, 10 ml of the suspension of afore-mentioned acetone precipitate were added, and the mixture was stirred at pH 8.5 at 37° C for 5 hours.

The resulting reaction solution was extracted three times with each 500 ml of n-butyl alcohol. These n-butyl alcohol layers were combined, evaporated to dryness under reduced pressure to obtain 9.8 g of the residue.

Then, said residue was dissolved in 90 ml of solvent mixture containing n-butyl alcohol, acetic acid, water and n-butyl-acetate in the ratios by volume of 4 : 1 : 1 : 4. The resulting solution was charged in a column filled with 500 g of silica gel, and then subjected to column chromatography by developing with the solvent mixture as above mentioned.

About 0.75 liters of the main fraction were evaporated to dryness under reduced pressure to obtain 0.7 g of residue. The residue was crystallized from ethyl alcohol to obtain 0.3 g of crude crystal. Said crude crystal was futher recrystallized from ethyl alcohol to obtain 0.17 g of DA-pepsidine in a form of white needles.

Melting point: Decomposed at 193° to 199° C, and clear melting point was not observed.

$[\alpha]_D^{20} = -57°$ to $-60°$ (C = 1; methanol)

Elementary analysis: for $C_{29}H_{55}N_5O_8 \cdot H_2O$

|  | C% | H% | N% |
|---|---|---|---|
| Calculated: | 56.19 | 9.26 | 11.29 |
| Found: | 56.39 | 8.99 | 11.27 |

EXAMPLE 2

Into 30 liter jar-fermentor, there were charged 15 liters of liquid nutrient medium (pH 7) containing 1% of meat extract, 1% of peptone and 0.5% of NaCl, and then the medium was sterilized at 120° 1 C for 10 minutes.

On the other hand, the broth of EF 49-210 strain was prepared by cultivating the bacterium at 30° C for 24 hours with shaking on the similar nutrient medium as afore-mentioned.

Into said jar-fermentor, 0.2 liters of the broth of said EF 49-210 strain were inoculated and the cultivation was carried out under the following conditions:

Time: 24 hours
Temperature: 30° C
Aeration: 15 liters per minute
Stirring: 350 r.p.m.

After accomplishment of the cultivation, the microorganisms were removed from the broth by centrifugation. Into 12 liters of the supernatant, ammonium sulfate was added to 0.8 saturation, and the mixture was placed in refrigeration for 3 days. The resulting precipitates were suspended in distilled water to obtain 750 ml of suspension.

A mixture of 100 ml of the suspension, 400 ml of the neutralized aqueous solution containing 8 g of pepsidine C, 292 ml of 1/15 M phosphate buffer (pH 5.5) and 8 ml of the solution of $CoCl_2$ (5 × $10^{-2}$M) was incubated for 40 hours at 37° C. The reaction mixture was extracted 3 times with 800 ml of n-butyl alcohol, respectively. The combined extracts were evaporated to dryness. The residue was dissolved in a minimum volume of the solvent mixture containing n-butyl alcohol, acetic acid, water and n-butyl acetate in the ratios by volume of 4 : 1 : 1 : 4, and was subjected to silicagel column chromatography with the similar solvent mixture as developing solvent.

Two liters of main fractions were combined and evaporated to dryness to give 6 g of white powder. The powder was crystallized twice from ethanol to give 2 g of DA-pepsidine in a form of white needles.

EXAMPLE 3

100 Mg of DA-pepsidine obtained by the process of Example 1 were dissolved in 10 ml of pyridine. 1.2 Ml of the 20-fold diluted acetylchloride solution in acetone were dropped into the above pyridine solution under ice-cooling. The mixture was allowed to stand overnight. An aliquot of this reaction mixture was subjected to silica gel thin layer chromatography by using the developing solvent containing n-butanol, acetic acid, water and n-butyl acetate in the ratios by volume of 4 : 1 : 1 : 4, followed by the detection of ninhydrin reaction, Rydon-Smith reaction, and casein plate method, whereby the resulting product exhibited Rf = 0.49, and it was identified with authentic pepsidine C.

The reaction solution was evaporated to dryness. The residue was dissolved in 10 ml of methanol. Into the resulting solution, 17 ml of ether solution of diazomethane were added. The solution was allowed to stand at room temperature for three hours, and then evaporated to dryness. The residue was dissolved in methanol. By the addition of ether, 34 mg of methylester of pepsidine C. were crystallized.

EXAMPLE 4

The procedure in Example 3 was repeated except that isovalerylchloride was used in place of acetylchloride. The product exhibits Rf = 0.64 on the thin layer chromatography identified with authentic pepstatin A.

EXAMPLE 5

One milliliter of the culture broth of EF 49-210 strain cultivated by the similar procedure as Example 1 was mixed with one milliliter of aqueous solution which was prepared by dissolving 10 mg of pepsidine C into water and neutralized by 6N NaOH solution. The resulting solution was shaked at 37° C for 5 hours.

The reaction solution was subjected to the silica gel thin layer chromatography by developing with the solvent containing n-butanol, acetic acid and water in the ratios by volume of 3 : 1 : 1. The product exhibits Rf = 0.48, and is identified with authentic DA-pepsidine.

EXAMPLE 6

The procedure in Example 5 was repeated except that pepsidine C was replaced with pepsidine B or pepsidine A. Formation of DA-pepsidine was detected with thin layer chromatography in the respective cases.

EXAMPLE 7

The procedure in Example 5 was repeated except that N-isovalerylpentapeptide (pepstatin A) was substituted for pepsidine C. There was also detected the formation of DA-pepsidine with thin layer chromatography.

EXAMPLE 8

The procedure in Example 5 was repeated, except that N-n-hexanoyl-pentapeptide or N-n-decanoyl-pentapeptide was repeated with pepsidine C. The production of DA-pepsidine as also confirmed with thin layer chromatography, in the respective cases.

EXAMPLE 9

The procedure in Example 5 was repeated except that Bacillus pumilus Kawaguchi EF 49-210 was replaced with Bacillus pumilus IFO 12092 or Bacillus pumilus IFO 12110. Formation of DA-pepsidine was detected with thin layer chromatography, in each case.

EXAMPLE 10

The procedure in Example 5 was repeated except that one milliliter of the culture broth of EF 49-210 strain was replaced 10 mg of acetone-dried cells of the bacterium. The formation of DA-pepsidine was detected with thin layer chromatography.

What is claimed is:

1. A process for the preparation of desacyl-pepsidine which comprises contacting an N-acyl-pentapeptide with a bacterium belonging to Bacillus pumilus.

2. The process as claimed in claim 2 wherein the reaction time ranges from about 3 to 60 hours.

3. The process as claimed in claim 2 wherein bacterium is Bacillus pumilus kawaguchi FE 49-210 (ATCC No. 31132 ).

4. The process as claimed in claim 2 wherein bacterium is Bacillus pumilus IFO-12092.

5. The process as claimed in claim 2 wherein bacterium is Bacillus pumilus IFO-12110.

6. The process as claimed in claim 2 wherein N-acyl-pentapeptide as the starting material is N-acyl-pentapeptide-containing material selected from the group consisting of culture filtrate of the microorganism which produces N-acyl-pentapeptide, products salted out from the culture filtrate, and dried products of an extract thereof by the use of an organic solvent.

7. The process as claimed in claim 1 wherein $Co^{++}$ compound is added.

8. The process as claimed in claim 1 wherein $CoCl_2$ or $CoSO_4$ is added.

9. The process as claimed in claim 1 wherein the bacterium is used in the form of its culture broth, culture filtrate, whole cell, dry cell or enzyme preparation thereof.

* * * * *

UNITED STATES PATENT OFFICE
CERTIFICATE OF CORRECTION

Patent No. 4,050,989          Dated September 27, 1977

Inventor(s) NORIAKI KUWANA ET AL.

It is certified that error appears in the above-identified patent and that said Letters Patent are hereby corrected as shown below:

Claims 2 to 6, line 1 of each, change "2" to --1--.

Signed and Sealed this

Seventh Day of March 1978

[SEAL]

Attest:

RUTH C. MASON
Attesting Officer

LUTRELLE F. PARKER
Acting Commissioner of Patents and Trademarks